(12) United States Patent
Couturier et al.

(10) Patent No.: US 9,096,490 B2
(45) Date of Patent: Aug. 4, 2015

(54) PROCESS FOR PREPARING SATURATED AMINO ACIDS OR SATURATED AMINO ESTERS COMPRISING A METATHESIS STEP

(75) Inventors: Jean Luc Couturier, Lyons (FR); Jean Luc Dubois, Millery (FR); Xiaowei Miao, Paris (FR); Cedric Fischmeister, Vignoc (FR); Christian Bruneau, Thorigne Fouillard (FR); Pierre Dixneuf, Rennes (FR)

(73) Assignees: ARKEMA FRANCE, Colombes (FR); UNIVERSITE DE RENNES 1, Rennes Cedex (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 143 days.

(21) Appl. No.: 13/696,712

(22) PCT Filed: May 9, 2011

(86) PCT No.: PCT/EP2011/002295
§ 371 (c)(1),
(2), (4) Date: Jan. 18, 2013

(87) PCT Pub. No.: WO2011/138051
PCT Pub. Date: Nov. 10, 2011

(65) Prior Publication Data
US 2013/0116458 A1  May 9, 2013

(51) Int. Cl.
| | | |
|---|---|---|
| C07C 227/04 | (2006.01) | |
| C11C 3/12 | (2006.01) | |
| C07C 229/08 | (2006.01) | |
| C07C 253/30 | (2006.01) | |
| B01J 31/22 | (2006.01) | |
| B01J 31/16 | (2006.01) | |

(52) U.S. Cl.
CPC ............ *C07C 227/04* (2013.01); *C07C 229/08* (2013.01); *C07C 253/30* (2013.01); *C11C 3/12* (2013.01); *B01J 31/1658* (2013.01); *B01J 31/2273* (2013.01)

(58) Field of Classification Search
None
See application file for complete search history.

(56) References Cited

U.S. PATENT DOCUMENTS

| | | | |
|---|---|---|---|
| 8,614,344 B2 * | 12/2013 | Kaido et al. ................ 554/145 |
| 2010/0168453 A1 | 7/2010 | Dubois | |
| 2011/0224454 A1 | 9/2011 | Dubois | |
| 2011/0300590 A1 | 12/2011 | Dubois | |

FOREIGN PATENT DOCUMENTS

| | | | | |
|---|---|---|---|---|
| WO | WO 2008/063322 | * | 5/2008 | ............. C07C 51/36 |
| WO | WO 2008/104722 A2 | | 9/2008 | |
| WO | WO 2010/055273 A1 | | 5/2010 | |
| WO | WO 2010/089512 A1 | | 8/2010 | |

OTHER PUBLICATIONS

International Search Report of PCT/EP2011/002295 (Sep. 22, 2011).

* cited by examiner

*Primary Examiner* — Yate K Cutliff
(74) *Attorney, Agent, or Firm* — Millen, White, Zelano & Branigan, P.C.

(57) ABSTRACT

The subject matter of the invention is a process for synthesizing a saturated long-chain α,ω-amino ester (acid) obtained in a first step by cross-metathesis between an acrylic first compound and a monounsaturated second compound comprising at least one nitrile, acid or ester trivalent function, one of these compounds comprising a nitrile function and the other an acid or ester function, in the presence of a ruthenium carbene metathesis catalyst, and in a second step by hydrogenation of the monounsaturated nitrile ester (acid) obtained in the presence of the metathesis catalyst of the preceding stop, acting as a hydrogenation catalyst.

13 Claims, No Drawings

PROCESS FOR PREPARING SATURATED AMINO ACIDS OR SATURATED AMINO ESTERS COMPRISING A METATHESIS STEP

The invention is targeted at a process for the synthesis of long-chain α,ω-aminoalkanoic acids or esters from a monounsaturated fatty acid or ester comprising at least one metathesis stage.

The polyamides industry, whether to manufacture synthetic fibers or thermosetting resins, uses a whole range of monomers consisting of diamines, diacids, and in particular long-chain ω-amino acids. The latter are normally referred to as Nylon, defined by the length of the methylene chain $(-CH_2-)_n$ separating two amide —CO—NH— functional groups. Thus it is that Nylon 6, Nylon 6-6, Nylon 6-10, Nylon 7, Nylon 8, Nylon 9, Nylon 11, Nylon 13, and the like, are known.

These monomers are generally manufactured by the chemical synthesis route using in particular, as starting materials, $C_2$ to $C_4$ olefins, cycloalkanes or benzene, hydrocarbons resulting from fossil sources, but also, in some specific cases, starting from castor oil (Nylon 11) or erucic oil (Nylon 13/13) or lesquerolic oil (Nylon 13).

Current developments in environmental matters are leading, in the fields of energy and chemistry, to the exploitation of natural starting materials originating from a renewable source being favored. This is the reason why some studies have been undertaken to develop, on the industrial scale, processes using fatty acids/esters as starting material for the manufacture of these monomers.

This type of approach has only a few industrial examples. One of the rare examples of an industrial process using a natural fatty acid as starting material is that of the manufacture, from ricinoleic acid extracted from castor oil, of 11-aminoundecanoic acid, which is the base for the synthesis of Rilsan 11®. This process is described in the work "Les Procédés de Pétrochimie" [Petrochemical Processes] by A. Chauvel et al. which appeared in Editions Technip (1986). 11-Aminoundecanoic acid is obtained in several stages. The first consists of a methanolysis of castor oil in a basic medium, producing methyl ricinoleate, which is subsequently subjected to a pyrolysis in order to obtain, on the one hand, heptanaldehyde and, on the other hand, methyl undecylenate. The latter is converted to the acid form by hydrolysis. Subsequently, the acid formed is subjected to a hydrobromination to give the ω-brominated acid, which is converted by ammoniation to 11-aminoundecanoic acid.

In this "bio" route, the main studies related to the synthesis of 9-aminononanoic acid, which is the precursor of Nylon 9, from oleic acid of natural origin.

As regards this specific monomer, mention may be made of the work "n-Nylons, Their Synthesis, Structure and Properties", 1997, published by J. Wiley and Sons, chapter 2.9 (pages 381 to 389) of which is devoted to Nylon 9. This article summarizes the achievements with regard to and the studies carried out on the subject. Mention is made therein, on page 381, of the process developed by the former Soviet Union which resulted in the commercialization of Pelargon®. Mention is also made therein, on page 384, of a process developed in Japan which uses oleic acid from soybean oil as starting material. The corresponding description refers to the work by A. Ravve, "Organic Chemistry of Macromolecules" (1967), Marcel Dekker, Inc., part 15 of which is devoted to polyamides and which mentions, on page 279, the existence of such a process.

For its part, the applicant company has carried out studies in this field. It has described, in the French patent application published under number FR 2912741, a process for the synthesis of a whole range of amino acids/esters of this type from a natural long-chain fatty acid/ester by subjecting the latter to a catalytic cross metathesis reaction with an unsaturated compound comprising a nitrile functional group, followed by a hydrogenation. In the French patent application filed on Nov. 17, 2008 under number FR 0857780, it also described a process for the synthesis of ω-aminoalkanoic acids or their esters from natural unsaturated long-chain fatty acids passing through an intermediate compound of ω-unsaturated nitrile type, one of the alternative forms of which employs, in the final phase, a cross metathesis of the ω-unsaturated nitrile with a compound of acrylate type. Finally, in the French patent application filed on Feb. 5, 2009 under number FR 0950704, it described an alternative form of the above process in which the intermediate compound is of the unsaturated dinitrile type. All these processes result in a final stage of hydrogenation of the nitrile functional group and of the double bond.

The object of the process of the invention is to improve the performance of processes employing, in the final phase, successively a cross metathesis and a hydrogenation. This is because it is important to be able to have available an efficient catalysis of these two successive reactions while minimizing the number of operations, which naturally has an effect on the final cost.

The hydrogenation of the nitrile functional group to give a primary amine is generally carried out on the industrial scale using highly reducing heterogeneous catalysts, such as Raney cobalt or nickel. The use of other metals known for their catalytic activity in hydrogenation has also been envisaged under heterogeneous conditions. Mention may be made, for example, of platinum, palladium, ruthenium or iridium, alone or in combination. Mention may be made, by way of illustration, of patent UK 1 177 154, which describes the use of various catalysts, Raney nickel, palladium or platinum, for the hydrogenation of the nitrile functional group of 11-cyanoundecanoic acid, and patent UK 1 273 874, which describes the use of a ruthenium catalyst deposited on silica for the same reaction, resulting in 12-aminododecanoic acid. However, nickel deposited on a support, such as silica, is the catalyst most generally adopted.

The homogeneous catalysis of this hydrogenation reaction of nitriles to give amines has also been the subject of studies and is described in the literature. Mention may be made, for example, of the hydrogenation of benzonitrile to give benzylamine with homogeneous ruthenium catalysts described by M. Hidai et al. in Organometallics, 2002, 21, 3897, and in the paper by R. H. Morris et al. in Organometallics, 2007, 26, 5940-5949, and in the paper by M. Beller et al. in ChemSusChem, 2008, 1, 1006; Chem. Eur. J., 2008, 14, 9491; Tetrahedron Lett., 2009, 50, 3654. The addition of a base in order to carry out this type of reaction is described in these papers.

The sequence of reactions, metathesis and then hydrogenation of the metathesis products, is described in patent application US 2009/048459 of Cargill, which describes a method for producing hydrogenated metathesis products with successive stages of metathesis and hydrogenation in which the hydrogenation stage is carried out by treating the metathesis reaction medium, containing the metathesis catalyst, using a heterogeneous hydrogenation catalyst consisting, according to all the examples, of supported nickel. It may also be specified that the reaction carried out in the examples is a homometathesis of soybean oil which results, due to the composition of this oil and the absence of any separation of the metathesis reaction products, in a complex mixture of esters and not in a monomer capable of being polymerized.

In point of fact, the applicant company has discovered that it is possible, in the process, to carry out the metathesis and hydrogenation stages using just one initial catalytic compound thus comprising the same active metal as catalyst. The metathesis catalyst, degraded at the end of the metathesis reaction, fulfils, during the second stage, the role of hydrogenation catalyst.

A subject matter of the invention is a process for the synthesis of a saturated long-chain α,ω-amino ester (acid) comprising from 6 to 17 carbon atoms, characterized in that it is obtained, in a first stage, by a cross metathesis reaction between a first acrylic compound, chosen from acrylonitrile, acrylic acid or an acrylic ester, and a second monounsaturated compound comprising at least one nitrile, acid or ester trivalent functional group, one of these compounds comprising a nitrile functional group and the other an acid or ester functional group, in the presence of a metathesis catalyst of ruthenium carbenes type, and, in a second stage, by the hydrogenation of the monounsaturated nitrile-ester (acid) obtained in the presence of the metathesis catalyst from the preceding stage acting as hydrogenation catalyst. The metathesis reaction under consideration is a cross metathesis reaction between a monounsaturated acid or ester compound, generally resulting from oleochemistry, with acrylonitrile, or a cross metathesis reaction between an unsaturated nitrile compound, generally resulting from oleochemistry, with an acrylic compound, an acid or acrylate, and, in this case, preferably methyl acrylate.

The process has been developed for the purpose of the exploitation of starting materials resulting from renewable natural sources. However, it can also clearly be applied to the analogous monounsaturated compounds obtained by chemical synthesis.

The metathesis stage is carried out according to the following reaction scheme:

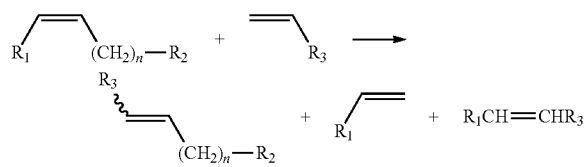

with $R_1$=H or $(CH_2)_m$—$R_4$,
$R_2$=COOR$_5$ or CN,
$R_3$=COOR$_5$ or CN,
$R_4$=H or $R_2$,
$R_5$=alkyl radical of 1 to 4 carbon atoms,
n=2 to 13,
m=4 to 11, and
$R_2$ is different from $R_3$.

The formula of the final α,ω-amino ester (acid) synthesized essentially depends on that of the compound which reacts with the acrylic compound.

In this compound resulting from oleochemistry, i.e. obtained from renewable natural fatty esters or acids, $R_1$ is either H or an alkyl radical or a functional alkyl radical comprising a trivalent functional group (CN, COOH or COOR).

$R_1$ will be H when the natural fatty ester will, for example, be subjected to an ethenolysis or, in some cases, to a pyrolysis. The formula of the α,ω-amino ester/acid obtained is then directly related to the —$(CH_2)_n$— radical of the fatty ester.

Thus it is that n will be equal to 7 with oleic acid, to 4 with petroselenic acid, to 8 from ricinoleic acid subjected to a pyrolysis, to 10 from lesquerolic acid subjected to a pyrolysis and the like, as is described in the French patent application published under number FR 2 912 741.

$R_1$ will be an alkyl radical when, in $(CH_2)_m$—$R_4$, $R_4$ is H. This corresponds to the use in the process of a monounsaturated natural fatty acid such as, for example, oleic acid, palmitoleic acid, petroselenic acid, lauroleic acid, and the like.

$R_1$ will be a functional alkyl radical when, in $(CH_2)_m$—$R_4$, $R_4$ is a radical representing a CN, COOH or COOR trivalent functional group which will be identical to $R_2$. The compound will then be in the diacid, diester or dinitrile form. It will then be particularly advantageous for the formula of the compound to exhibit a symmetry which makes it possible to optimize the yields of final α,ω-amino ester/acid. The production of compounds of this type, in particular by metathesis, is described in the abovementioned applications FR 2912741, FR 0857780 and FR 0950704.

As regards the acrylic compound, the choice of the trivalent functional group $R_3$ is related to the nature of the trivalent functional group of the other compound, $R_3$ having to be nitrile when $R_2$ is ester/acid and conversely ester/acid when $R_2$ is nitrile.

This reaction results in unsaturated nitrile-acids or nitrile-esters.

Preferably, the cross metathesis reaction with acrylonitrile is carried out with a compound chosen from 9-decenoic acid or methyl 9-decenoate, resulting from the ethenolysis of oleic acid or methyl oleate, 10-undecenoic acid or methyl 10-undecenoate, resulting from the cracking of ricinoleic acid or methyl ricinoleate, oleic acid or methyl oleate, 9-octadecenedioic acid or methyl 9-octadecenedioate, resulting from the homometathesis or fermentation of oleic acid, erucic acid and methyl erucate, or 12-tridecenoic acid or methyl 12-tridecenoate, resulting from lesquerolic acid.

The cross metathesis reaction of the acrylic ester (acid) is carried out with a compound chosen from 9-decenenitrile, resulting from 9-decenoic acid, 10-undecenenitrile, resulting from 10-undecenoic acid, 9-octadecenenitrile or oleonitrile, resulting from oleic acid, 9-octadecenedinitrile, resulting from 9-octadecenedioic acid, eruconitrile or 12-tridecenonitrile, resulting from lesquerolic acid.

The cross metathesis reaction with a compound of acrylic type is carried out under conditions which are fully known. The metathesis reaction is preferably carried out at a reaction temperature of between 20 and 120° C. and under a pressure of between 1 and 30 bar, in the presence of a ruthenium-based catalyst. It will preferably be carried out at a low pressure of between and 10 bar and more preferably at atmospheric pressure when the cross metathesis results in the formation of a light compound, for example ethylene, in order to make possible easy release thereof. The reaction can be carried out without solvent or in the presence of a solvent, such as toluene, xylenes or dichloromethane, benzene, chlorobenzene or dimethyl carbonate.

The catalysis of the metathesis reaction has been the subject of a great many studies and the development of sophisticated catalytic systems. Mention may be made, for example, of the tungsten complexes developed by Schrock et al. (J. Am. Chem. Soc., 108 (1986), 2771) or Basset et al., Angew. Chem., Ed. Engl., 31 (1992), 628.

"Grubbs'" catalysts have more recently appeared (Grubbs et al., Angew. Chem., Ed. Engl., 34 (1995), 2039, and Organic Letters 1 (1999), 953), which are ruthenium-benzylidene complexes operating in homogeneous catalysis.

Finally, studies have been carried out for the preparation of immobilized catalysts, that is to say, catalysts having an active principle which is that of the homogeneous catalyst, in particular ruthenium-carbene complexes, but which is immobilized on an inactive support. The objective of these studies is to increase the selectivity of the cross metathesis reaction with regard to side reactions, such as "homometatheses" between the reactants brought together. They relate not only to the structure of the catalysts but also to the effect of the reaction medium and the additives which may be introduced.

The ruthenium catalysts are preferably chosen from charged or uncharged catalysts of general formula: $(X1)_a(X2)_b$ Ru(carbene C)$(L1)_c(L2)_d(L3)_e$ in which:

a, b, c, d and e are identical or different integers, with a and b equal to 0, 1 or 2; c, d and e equal to 0, 1, 2, 3 or 4;

X1 and X2, which are identical or different, each represent a charged or uncharged and monochelating or polychelating ligand; mention may be made, by way of examples, of halides, sulfate, carbonate, carboxylates, alkoxides, phenolates, amides, tosylate, hexafluorophosphate, tetrafluoroborate, bis(triflyl)amide, an alkyl, tetraphenylborate and derivatives. X1 or X2 can be bonded to (L1 or L2) or to the (carbene C) so as to form a bidentate or chelate ligand on the ruthenium; and L1, L2 and L3, which are identical or different, are electron-donating ligands, such as phosphine, phosphite, phosphonite, phosphinite, arsine, stilbene, an olefin or an aromatic compound, a carbonyl compound, an ether, an alcohol, an amine, a pyridine or derivative, an imine, a thioether or a heterocyclic carbene;

L1, L2 or L3 can be bonded to the (carbene C) so as to form a bidentate or chelate ligand, or a tridentate ligand;

the (carbene C) being represented by the general formula: $C_=(R1)_=(R2)$, for which R1 and R2 are identical or different groups, such as hydrogen or any other saturated or unsaturated and cyclic, branched or linear hydrocarbon group or aromatic hydrocarbon group. Mention may be made, by way of examples, of ruthenium alkylidene, benzylidene or cumulene complexes, such as vinylidenes Ru=C=CHR or allenylidenes Ru=C=C=CR1R2 or indenylidenes.

A functional group which makes it possible to improve the retention of the ruthenium complex in an ionic liquid can be grafted to at least one of the ligands X1, X2, L1 or L2 or to the carbene C. This functional group can be charged or uncharged, such as, preferably, an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The metathesis catalyst can optionally be rendered heterogeneous on a support in order to facilitate the recovery/recycling thereof.

The cross metathesis catalysts of the process of the invention are preferably ruthenium carbenes described, for example, in Aldrichimica Acta, Vol. 40, No. 2, 2007, pp. 45-52. The preferred catalysts are the catalyst Umicore M51 (sold by Umicore) of formula (A) below, and the 2nd generation Hoveyda-Grubbs catalyst, also known as Hoveyda II (sold by Sigma-Aldrich), of formula (B) below.

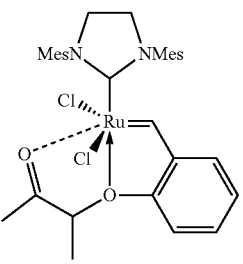

(A)

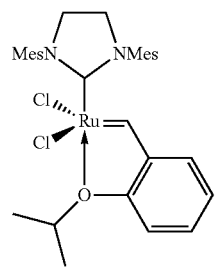

(B)

The reaction time is chosen as a function of the reactants and operating conditions employed and in order to reach the end of the reaction.

As the metathesis is an equilibrium reaction, it is advisable to shift this equilibrium in order to proceed towards total conversion. In order to do this in the case where the co-product of the reaction is a light olefin, such as ethylene, it is easy to "degas" the reactor from time to time in order to force the removal of the light products and thus to proceed towards total conversion. In the case where the co-product is a heavier olefin, optionally a functional one, the extraction operation is more problematic insofar as it is necessary to keep the two reactants and the catalyst in the reaction medium. Furthermore, if it is necessary to separate, at least in part, the unsaturated nitrile-ester (acid) by distillation and to remove the light products before the hydrogenation, the operation has to be carried out so that the metathesis catalyst remains in the heavy fraction with the nitrile-ester (acid) in order to use it in its role of hydrogenation catalyst. In this operation, during the separation, the very heavy compounds are not removed from the medium, which compounds would thus be hydrogenated with the heavy fraction, their separation occurring during a subsequent purification of the final amino acid/ester.

The other way of shifting the equilibrium is to use an excess of reactant, typically in this instance an excess of acrylonitrile or alkyl acrylate (generally methyl acrylate). From a processing viewpoint, the first stage would be carried out to completion with the exhausting of the metathesis catalyst, the excess acrylate or acrylonitrile would be distilled for recycling, and then, in a second stage, the unsaturated α,ω-nitrile-ester/acid compound present in the reaction medium would be hydrogenated in the presence of the metal of the catalyst of the 1st stage in its hydrogenation role.

The amount of ruthenium metathesis catalyst introduced during the first stage is chosen so that it ensures all the possible conversion of the nonacrylic reactant present in the charge. It is observed that said catalyst, under the operating conditions of the metathesis stage, is converted after the reaction; it is exhausted or deactivated and loses its catalytic activity after metathesis - it will be subsequently denoted by the term "degraded" for said reaction. In the batch process, the amount of catalyst can easily be adjusted in order to give the desired conversion at complete degradation of the catalyst.

After the metathesis stage, the reaction medium comprising the ruthenium is thus subjected to a hydrogenation. The ruthenium metathesis catalyst is degraded on completion of the metathesis stage but the metal is still present in the reaction medium in a form appropriate for the hydrogenation stage.

The hydrogenation reaction is thus directly carried out on the reaction mixture resulting from the metathesis stage and in the presence of the residual metathesis catalyst acting as hydrogenation catalyst, under a hydrogen pressure and in the presence of a base. The pressure is between 5 and 100 bar, preferably between 20 and 30 bar. The temperature is between 50 and 150° C., preferably between 80 and 100° C. The base can be, for example, sodium hydroxide, potassium hydroxide, potassium tert-butoxide or ammonia. The base is generally used at a content of 10 to 80 mol % with respect to the unsaturated nitrile-ester substrate.

The hydrogenation reaction can be carried out with or without solvent. In the case of a reaction in a solvent medium, the preferred solvents used for the metathesis and hydrogenation stages are aromatic solvents, such as toluene or xylenes, or a chlorinated solvent, such as dichloromethane or chlorobenzene, or dimethyl carbonate.

On conclusion of this hydrogenation stage carried out without a specific hydrogenation catalyst, the degree of conversion of the nitrile functional group to give a primary amine is particularly high, even without addition of $NH_3$, and also, of course, the reduction of the olefinic unsaturation, without the carboxyl functional group having been affected.

It is thus shown, unexpectedly, that the degraded metathesis catalyst exhibited activity and selectivity for the hydrogenation of the unsaturated nitrile-acids or nitrile-esters to give saturated amino acids or amino esters.

The degraded metathesis catalyst can optionally be employed with, in addition, a conventional hydrogenation catalyst for the hydrogenation stage. Mention may be made, among the metals conventionally used for the hydrogenation, of nickel, palladium, platinum, rhodium or iridium. Preferably, the degraded metathesis catalyst might be supplemented by Raney nickel or palladium-on-charcoal.

Thus, in a specific embodiment, the hydrogenation reaction is carried out in the presence of the degraded metathesis catalyst resulting from the first stage supplemented by a conventional hydrogenation catalyst.

It can also be employed in the presence of a solid support (charcoal, SiC, and the like) in order to simplify its recovery.

The amino acids or amino esters obtained according to the process of the invention can be used as monomers in the synthesis of polyamides.

A further subject matter of the invention is polymers obtained by polymerization of the α,ω-amino esters (acids) synthesized according to the processes defined above.

The process of the invention is illustrated by the following examples.

Example 1

Cross metathesis of methyl undecenoate with acrylonitrile, followed by hydrogenation, with the Hoveyda-Grubbs II catalyst:

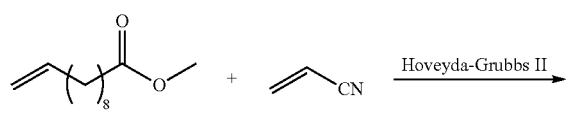

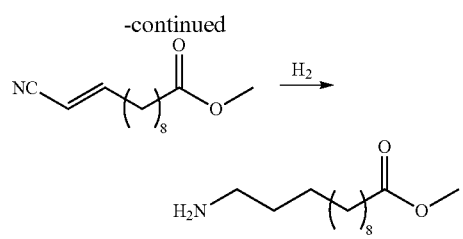

100 mg of methyl 10-undecenoate (0.5 mmol), 53 mg of acrylonitrile (1 mmol) and 10 ml of toluene distilled over sodium benzophenone are charged to a 50 ml Schlenk tube purged with nitrogen. 9.5 mg of 2nd generation Hoveyda-Grubbs catalyst ($1.5 \times 10^{-2}$ mmol, supplier Sigma-Aldrich) are added and the mixture is heated at 100° C. for 4 hours.

The gas chromatography analysis shows that the conversion of the methyl 10-undecenoate is 100 mol % (96 mol %) and that the yield of unsaturated nitrile-ester is 95 mol %.

The reaction mixture is then transferred into a 50 ml Parr bomb (22 ml). 17 mg of potassium hydroxide (0.3 mmol) are added and the bomb is pressurized under 20 bar of hydrogen. It is heated at 80° C. for 48 h with magnetic stirring.

The gas chromatography analysis shows that the conversion of the unsaturated nitrile-ester is 100 mol % and that the yield of methyl 12-aminododecanoate is 90 mol %.

Example 2

Cross metathesis of methyl undecenoate with acrylonitrile, followed by hydrogenation, with Umicore M51 catalyst:

The procedure is the same as in example 1, the Hoveyda-Grubbs II catalyst being replaced with 10 mg of Umicore M51 catalyst ($1.5 \times 10^{-2}$ mmol, supplier Umicore), and the potassium hydroxide being replaced with 8.5 mg of potassium tert-butoxide (0.075 mmol).

The gas chromatography analysis shows that the yield of methyl 12-aminododecanoate is 88 mol %.

Example 3

Undecenenitrile/methyl acrylate cross metathesis, followed by hydrogenation, with the Hoveyda-Grubbs II catalyst:

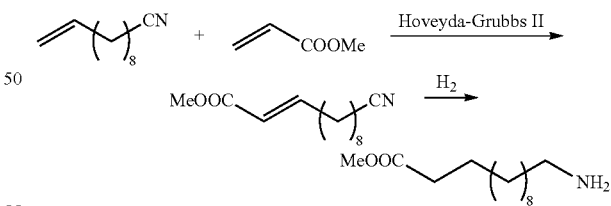

83 mg of 10-undecenenitrile (0.5 mmol), 86 mg of methyl acrylate (1 mmol) and 10 ml of toluene distilled over sodium benzophenone are charged to a 50 ml Schlenk tube purged with nitrogen. 9.5 mg of 2nd generation Hoveyda-Grubbs catalyst ($1.5 \times 10^{-2}$ mmol) are added and the mixture is heated at 100° C. for 1 hour.

The gas chromatography analysis shows that the conversion of the 10-undecenenitrile is 100% and that the yield of unsaturated nitrile-ester is 98%.

The reaction mixture is then transferred into a 50 ml Parr bomb (22 ml). 17 mg of potassium tert-butoxide (0.15 mmol)

are added and the bomb is pressurized under 20 bar of hydrogen. The bomb is heated at 80° C. for 40 h with magnetic stirring.

The gas chromatography analysis shows that the conversion of the unsaturated nitrile-ester is 100 mol % and that the yield of methyl 12-aminododecanoate is 90 mol %.

Example 4

Methyl undecenoate/acrylonitrile cross metathesis with Hoveyda-Grubbs II catalyst, followed by hydrogenation, with supplementary addition of Pd/C catalyst:

100 mg of methyl 10-undecenoate (0.5 mmol), 53 mg of acrylonitrile (1 mmol) and 10 ml of toluene distilled over sodium benzophenone are charged to a 50 ml Schlenk tube purged with nitrogen. 3 mg of 2nd generation Hoveyda-Grubbs catalyst ($5 \times 10^{-3}$ mmol) are added and the mixture is heated at 100° C. for 4 hours.

The gas chromatography analysis shows that the conversion of the methyl 10-undecenoate is 98% and that the yield of unsaturated nitrile-ester is 93%.

The reaction mixture is then transferred into a 50 ml Parr bomb (22 ml). 10 mg of 1% Pd/C catalyst and 17 mg of potassium tert-butoxide (0.15 mmol) are added and the bomb is pressurized under 20 bar of hydrogen. The bomb is heated at 80° C. for 48 h with magnetic stirring.

The gas chromatography analysis shows that the conversion of the unsaturated nitrile-ester is 90% and that the yield of methyl 12-aminododecanoate is 64%.

The invention claimed is:

1. A process for the synthesis of a saturated long-chain α,ω-amino ester (acid) comprising from 6 to 17 carbon atoms, comprising, first, a cross metathesis reaction between a first acrylic compound, that is acrylonitrile, acrylic acid or an acrylic ester, and a second monounsaturated compound comprising at least one nitrile, acid or ester trivalent functional group, one of these compounds comprising a nitrile functional group and the other an acid or ester functional group, in the presence of a ruthenium carbenes metathesis catalyst, and, second, hydrogenation of monounsaturated nitrile-ester (acid) obtained in the presence of the metathesis catalyst from the cross metathesis reaction acting as hydrogenation catalyst.

2. The process as claimed in claim 1, wherein the metathesis is carried out according to the following reaction scheme:

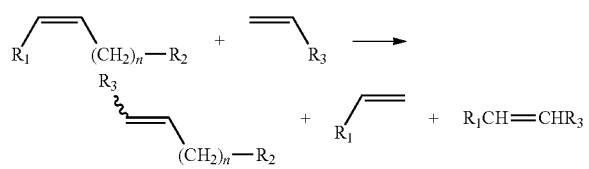

with
$R_1$=H or $(CH_2)_m$—$R_4$,
$R_2$=COOR$_5$ or CN,
$R_3$=COOR$_5$ or CN,
$R_4$=H or $R_2$,
$R_5$=alkyl radical of 1 to 4 carbon atoms,
n=2 to 13, m=4 to 11, and
$R_2$ is different from $R_3$.

3. The process as claimed in claim 1, wherein the cross metathesis reaction with acrylonitrile is carried out with 9-decenoic acid, methyl 9-decenoate, 10-undecenoic acid, methyl 10-undecenoate, oleic acid, methyl oleate, 9-octadecenedioic acid, methyl 9-octadecenedioate, erucic acid, methyl erucate, 12-tridecenoic acid or methyl 12-tridecenoate.

4. The process as claimed in claim 1, wherein the cross metathesis reaction of the acrylic ester (acid) is carried out with 9-decenenitrile, 10-undecenenitrile, 9-octadecenenitrile or oleonitrile, 9-octadecenedinitrile, eruconitrile or 12-tridecenonitrile.

5. The process as claimed in claim 1, wherein the metathesis reaction is carried out at a reaction temperature of between 20 and 120° C. and under a pressure of between 1 and 30 bar.

6. The process as claimed in claim 1, wherein the metathesis reaction is carried out in the presence of a charged or uncharged ruthenium catalyst of formula:

$(X1)_a(X2)_b Ru(\text{carbene } C)(L1)_c(L2)_d(L3)_e$ in which:
a, b, c, d and e are identical or different integers, with a and b equal to 0, 1 or 2; c, d and e equal to 0, 1, 2, 3 or 4;
X1 and X2, which are identical or different, each represent a charged or uncharged and monochelating or polychelating ligand, X1 or X2 can be bonded to Y1 or Y2 (L1 or L2) or to the (carbene C) so as to form a bidentate or chelate ligand on the ruthenium; and
L1, L2 and L3, which are identical or different, are electron-donating ligands, it being possible for L1, L2 or L3 to be bonded to the (carbene C) so as to form a bidentate or chelate ligand, or a tridentate ligand, the (carbene C) being represented by the formula:
C_(R1)_(R2), for which R1 and R2 are identical or different and are hydrogen or any other saturated or unsaturated and cyclic, branched or linear hydrocarbonyl group or aromatic hydrocarbonyl group.

7. The process as claimed in claim 6, wherein the metathesis catalyst corresponds to either of the formulae (A) and (B) below:

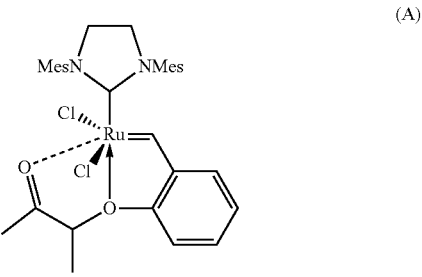

(A)

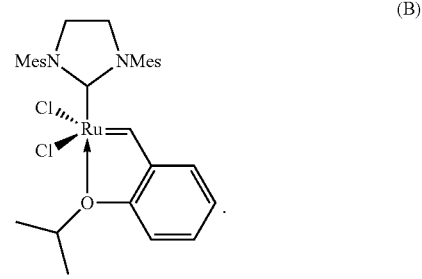

(B)

8. The process as claimed in claim 1, wherein the hydrogenation reaction is carried out on the reaction mixture resulting from the metathesis and in the presence of the residual metathesis catalyst acting as hydrogenation catalyst, under hydrogen pressure and in the presence of a base.

9. The process as claimed in claim 1, wherein the hydrogenation reaction is carried out at a pressure of 5 and 100 bar, and at a temperature of between 50 and 150° C.

10. The process as claimed in claim 1, wherein the hydrogenation reaction is carried out in the presence of a sodium hydroxide, potassium hydroxide, potassium tert-butoxide or ammonia base, at a content of 10 to 80 mol % with respect to the unsaturated nitrile-ester substrate.

11. The process as claimed in claim 1, wherein the hydrogenation reaction is carried out in the presence of the degraded metathesis catalyst resulting from the first stage supplemented by a conventional hydrogenation catalyst.

12. The process according to claim 6, wherein X1 and X2 are each independently halides, sulfate, carbonate, carboxylates, alkoxides, phenolates, amides, tosylate, hexafluorophosphate, tetrafluoroborate, bis(triflyl)amide, or tetraphenylborate.

13. The process according to claim 6, wherein L1, L2 and L3 are each independently phosphine, phosphite, phosphonite, phosphinite, arsine, stilbene, an olefin, an aromatic compound, a carbonyl compound, an ether, an alcohol, an amine, a pyridine, an imine, a thioether or a heterocyclic carbine.

* * * * *